(12) United States Patent
Okoniewski et al.

(10) Patent No.: US 9,615,893 B2
(45) Date of Patent: Apr. 11, 2017

(54) SEAL CLEANING OBTURATOR (71) Applicant: Covidien LP, Mansfield, MA (US)

(72) Inventors: Gregory G. Okoniewski, North Haven, CT (US); Anibal Rodrigues, Jr., Milford, CT (US)

(73) Assignee: Covidien LP, Mansfield, MA (US)

( * ) Notice: Subject to any disclaimer, the term of this patent is extended or adjusted under 35 U.S.C. 154(b) by 665 days.

(21) Appl. No.: 14/064,471

(22) Filed: Oct. 28, 2013

(65) Prior Publication Data

US 2014/0135740 A1    May 15, 2014

Related U.S. Application Data (60) Provisional application No. 61/726,185, filed on Nov. 14, 2012.

(51) Int. Cl.
    *A61B 90/70*     (2016.01)
    *A61B 17/34*     (2006.01)

(52) U.S. Cl.
    CPC .......... *A61B 90/70* (2016.02); *A61B 17/3462* (2013.01); *A61B 2017/3437* (2013.01); *A61B 2217/005* (2013.01)

(58) Field of Classification Search
    CPC . A61B 19/34; A61B 17/3462; A61B 17/3421; A61B 17/3423; A61B 2017/3437; A61B 2217/005
    See application file for complete search history.

(56) References Cited

U.S. PATENT DOCUMENTS

| | | | |
|---|---|---|---|
| 958,854 A | 5/1910 | Bunn | |
| 4,889,106 A | 12/1989 | Watanabe | |
| 4,894,056 A | 1/1990 | Bommarito | |
| 5,030,213 A | 7/1991 | Rumberger et al. | |
| 5,168,593 A | 12/1992 | Poje et al. | |
| 5,240,675 A | 8/1993 | Wilk et al. | |
| 5,251,356 A | 10/1993 | Oaki et al. | |
| 5,297,310 A | 3/1994 | Cox et al. | |
| 5,382,297 A | 1/1995 | Valentine et al. | |
| 5,439,457 A | 8/1995 | Yoon | |
| 5,615,439 A | 4/1997 | Bourrelly | |
| 5,709,691 A | 1/1998 | Morejon | |

(Continued)

FOREIGN PATENT DOCUMENTS

WO      2007034202 A1     3/2007

OTHER PUBLICATIONS

Extended European Search Report, corresponding to European Application No. 13192651.1, dated Feb. 24, 2014; 6 pages.

*Primary Examiner* — Michael Kornakov
*Assistant Examiner* — Natasha Campbell (57) ABSTRACT

A surgical instrument configured for insertion through a surgical access device including a seal member is disclosed. The surgical instrument includes an elongate body having a central passageway extending at least partially therethrough and a plurality of slots extending radially outward from the central passageway. The plurality of slots are configured to engage the seal member and the surgical access device when the elongate body is translated therethrough to remove debris from the seal member and the surgical access device. The plurality of slots and the central passageway are configured to retain the removed debris therein during withdrawal of the surgical instrument from the surgical access device.

17 Claims, 13 Drawing Sheets

(56) References Cited

U.S. PATENT DOCUMENTS

| | | |
|---|---|---|
| 5,814,160 A | 9/1998 | Orlando |
| 5,964,004 A | 10/1999 | Bean |
| 6,045,623 A | 4/2000 | Cannon |
| 6,183,450 B1 | 2/2001 | Lois |
| 6,679,262 B1 | 1/2004 | Morejon |
| 6,699,331 B1 | 3/2004 | Kritzler |
| 6,920,662 B2 | 7/2005 | Moore |
| 2003/0213501 A1 | 11/2003 | Thomson et al. |
| 2004/0154115 A1 | 8/2004 | Schultz |
| 2004/0181194 A1 | 9/2004 | Perkins |
| 2004/0187893 A1 | 9/2004 | Maguire, Jr. et al. |
| 2005/0171493 A1 | 8/2005 | Nicholls |
| 2006/0130847 A1* | 6/2006 | Morejon ........... A61M 16/0463 128/207.15 |
| 2006/0162105 A1 | 7/2006 | Abe |
| 2006/0191087 A1 | 8/2006 | Maguire, Jr. et al. |
| 2008/0058852 A1 | 3/2008 | Ihde |
| 2008/0098543 A1 | 5/2008 | Esquenet et al. |
| 2008/0141473 A1 | 6/2008 | Arai et al. |
| 2009/0007352 A1 | 1/2009 | Komine et al. |
| 2009/0044353 A1 | 2/2009 | Galantai et al. |
| 2009/0113644 A1 | 5/2009 | Heck |
| 2009/0118586 A1 | 5/2009 | Griffin |
| 2009/0178674 A1 | 7/2009 | Schnell |
| 2009/0250081 A1 | 10/2009 | Gordin et al. |
| 2010/0012152 A1 | 1/2010 | Hansen |
| 2010/0065083 A1 | 3/2010 | Soetermans |
| 2010/0139018 A1 | 6/2010 | Maslanka |
| 2010/0163073 A1 | 7/2010 | Lyngstadaas et al. |
| 2011/0230853 A1 | 9/2011 | Ihde, II |

\* cited by examiner

SEAL CLEANING OBTURATOR

CROSS-REFERENCE TO RELATED APPLICATIONS

This application claims the benefit of and priority to U.S. Provisional Patent Application No. 61/726,185, filed Nov. 14, 2012, the entire disclosure of which is incorporated by reference herein.

BACKGROUND

Technical Field

The present disclosure relates generally to a surgical instrument for insertion through an access device having a seal member and, more particularly, to a surgical instrument configured to remove debris from the access device and the seal member.

Description of Related Art

During laparoscopic, endoscopic, arthroscopic, and other similar surgical procedures, surgical instruments are typically inserted through a cannula, trocar or other access device into the body to perform a desired surgical task. Often, multiple instruments are inserted through and removed from the same access device over the course of a procedure. Body fluids and/or other debris, however, may accompany a surgical instrument as it is being withdrawn from the surgical site. The body fluids and debris may be deposited onto the access device or may become lodged against a seal or other sealing member of the access device. Surgical devices which are subsequently inserted through the access device, such as, for example, an endoscope, obturator, etc, may become may become fouled by the body fluids or debris, thereby reducing their effectiveness and potentially increasing the duration of the procedure. The body fluids or other debris, for example, may become smeared on the endoscope, thereby occluding the surgeon's ability to observe the surgical site. This may require the surgeon to remove, clean and re-insert the endoscope one or more times to obtain a clear image.

SUMMARY

In the drawings, and in the following description, the term "proximal" should be understood as referring to the end of the pertinent structure that is closer to the clinician during proper use, while the term "distal" should be understood as referring to the end that is farther from the clinician, as is traditional and conventional in the art.

In an aspect of the present disclosure, a surgical instrument configured for insertion through a surgical access device including a seal member is disclosed. The surgical instrument includes an elongate body having a central passageway extending at least partially therethrough and a plurality of slots extending radially outward from the central passageway. The plurality of slots are configured to engage the seal member and the surgical access device when the elongate body is translated therethrough to remove debris from the seal member and the surgical access device. The plurality of slots and the central passageway are configured to retain the removed debris therein during withdrawal of the surgical instrument from the surgical access device.

In an aspect of the present disclosure, the surgical instrument includes an insert member configured for removable insertion into the central passageway of the elongate member. The insert member is configured to retain the removed debris within the passageway. The insert member may be formed from an absorbent material that is configured to absorb and retain the debris therein.

In an aspect of the present disclosure, the central passageway extends through a proximal end of the elongate body.

In an aspect of the present disclosure, the surgical instrument further includes a suction mechanism fluidly coupleable to a vacuum source and disposed in fluid communication with the central passageway of the elongate body. The suction mechanism is configured to draw debris into the plurality of slots and the central passageway.

In an aspect of the present disclosure, the elongate body includes a seal member adjacent a distal portion thereof. The seal member may be an umbrella seal that is transitionable between a deployed condition and a collapsed condition and may include at least one strut. The at least one strut is configured to transition the umbrella seal between the deployed condition and the collapsed condition. The surgical instrument may include an actuation mechanism operatively associated with the umbrella seal and configured to transition the umbrella seal between the deployed condition and the collapsed condition. The actuation mechanism may include a cable attached to the umbrella seal and actuatable to transition the umbrella seal between the deployed condition and the collapsed condition. A proximal end of the umbrella seal may be spaced from the elongate body when the umbrella seal is in the deployed condition.

In an aspect of the present disclosure, the surgical instrument further includes a sealing cap that is configured to fluidly seal a proximal end of the central passageway.

In an aspect of the present disclosure, the slots extend from the central passageway in a plurality of rows. The slots of a first of the rows may be rotationally offset relative to the slots of a second of the rows. The first and second rows may be adjacent.

In an aspect of the present disclosure, a method of cleaning a surgical access device including a seal member is disclosed. The method includes the steps of inserting a surgical instrument including an elongate body having a central passageway and a plurality of slots extending radially outward from the central passageway into a lumen of the surgical access device, receiving debris from the lumen of the surgical access device in at least one of the slots and retaining the removed debris in the at least one of the slots, and withdrawing the surgical instrument from the surgical access device such that the at least one of the slots engages a distal surface of the seal member to remove debris from the distal surface of the seal member. The removed debris may be retained within the at least one of the slots of the elongate body during withdrawal of the surgical instrument from the surgical access device.

In an aspect of the present disclosure, the step of receiving debris includes receiving debris through the at least one of the slots into the central passageway and retaining the debris in the central passageway.

In an aspect of the present disclosure, the method further includes the step of inserting an absorbent insert into the central passageway. The absorbent insert may be configured to receive and absorb debris from the seal member and the surgical access device.

In an aspect of the present disclosure, the surgical instrument further includes a suction mechanism in fluid communication with the central passageway and the step of receiving and retaining debris may including applying a vacuum to the at least one of the slots and the central passageway to draw the debris into the at least one of the slots and the passageway.

In an aspect of the present disclosure, the surgical instrument may include a sealing member adjacent a distal portion thereof. The method may further include the step of actuating the sealing member to transition the sealing member between a deployed condition and a collapsed condition.

It is contemplated that any of the above-mentioned aspects may be included with any of the above-mentioned embodiments. It is further contemplated that any of the above embodiments may be combined.

BRIEF DESCRIPTION OF THE DRAWINGS

The accompanying drawings, which are incorporated in and constitute a part of this specification, illustrate embodiments of the present disclosure and, together with a general description of the present disclosure given above, and the detailed description of the embodiments given below, serve to explain the principles of the present disclosure.

DETAILED DESCRIPTION

Various embodiments of the presently disclosed surgical instrument, and methods of using the same, will now be described in detail with reference to the drawings wherein like references numerals identify similar or identical elements. In the drawings, and in the following description, the term "proximal" should be understood as referring to the end of the pertinent structure that is closer to the clinician during proper use, while the term "distal" should be understood as referring to the end that is farther from the clinician, as is traditional and conventional in the art. As used herein, the term "debris" includes both solid and fluid matter and includes a patient's body fluids or body matter and also externally introduced fluids and matter.

Figure 1:
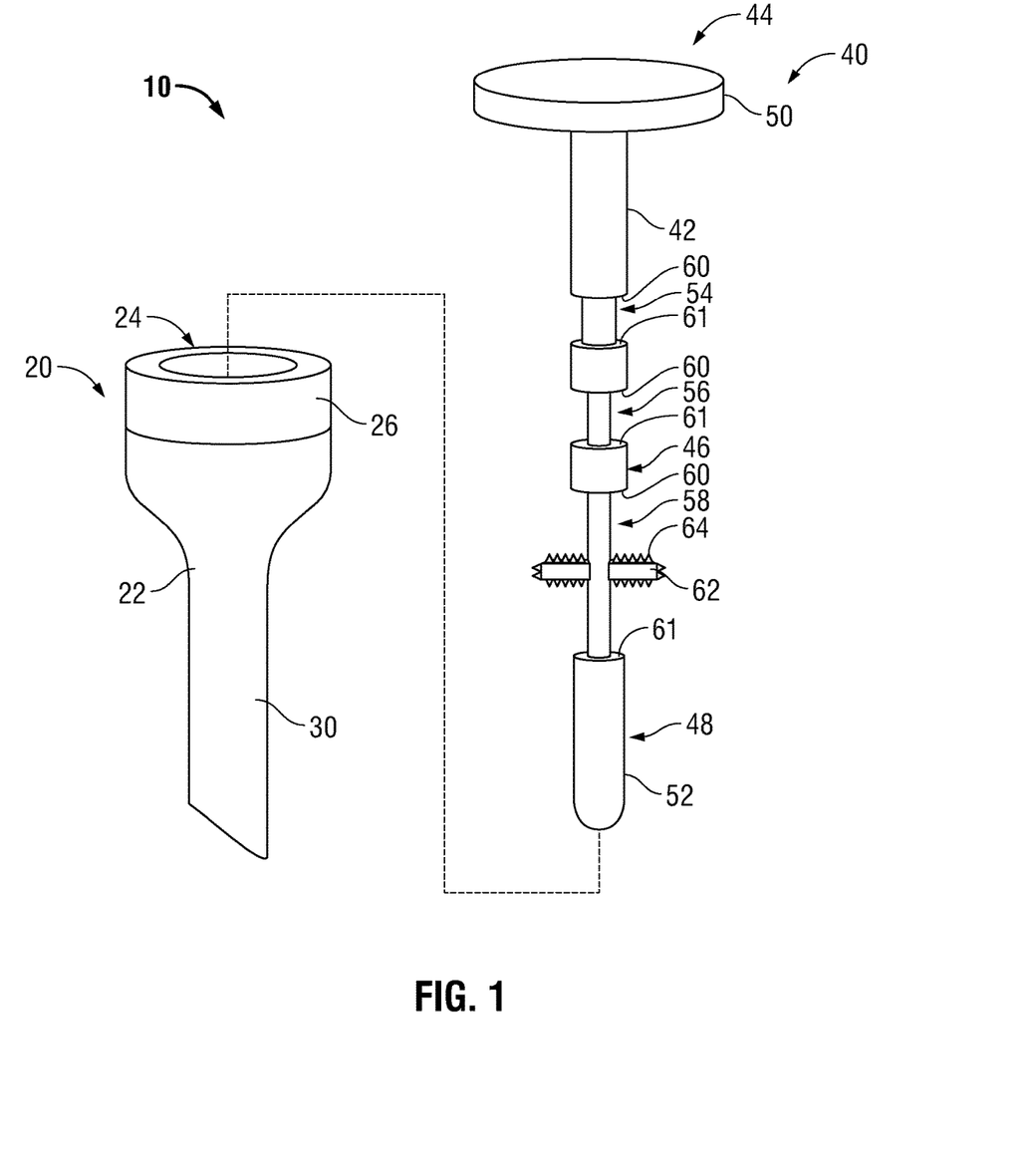
FIG. 1 is a perspective view illustrating an access system in accordance with the present disclosure.
Figure 2:
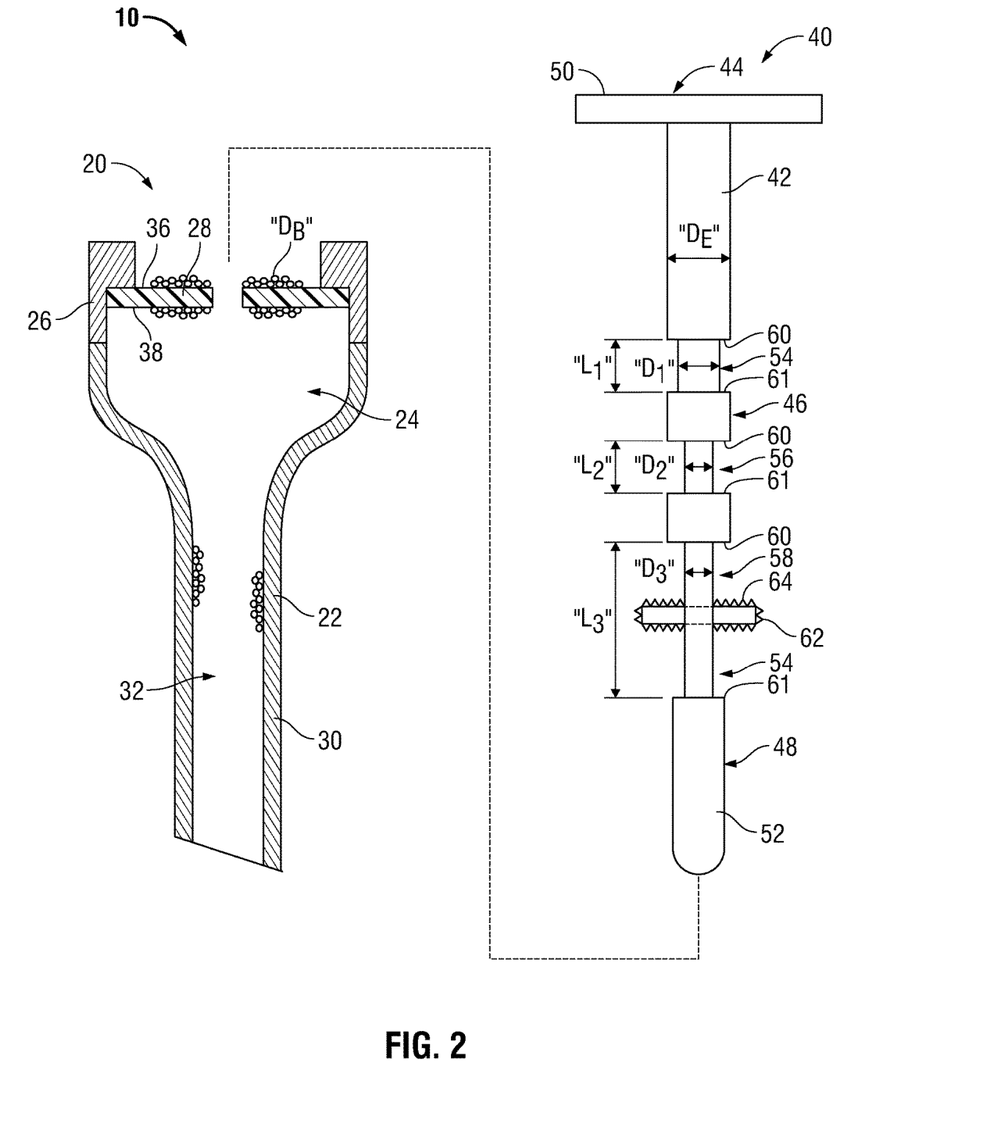
FIG. 2 is a side, partial cross-sectional view of the access system of FIG. 1.

Referring now in detail to the drawing figures, and in particular initially to FIGS. 1 and 2, a surgical access system is generally shown as 10. Surgical access system 10 includes an access device 20 and an obturator member 40 configured for insertion through access device 20. Access device 20 includes a housing body 22 defining a longitudinal passageway 24 extending therethrough. Housing body 22 includes a proximal portion 26 having a seal member 28 disposed therein and a distal portion 30 defining an elongate shaft 32. In one embodiment, proximal portion 26 defines a larger diameter than distal portion 30. Proximal portion 26 may also be tapered toward distal portion 30. Access device 20 may be any kind of trocar or access device as known in the art. Seal member 28 may be a zero-seal, septum seal, or any other similar seal known in the art that is configured to receive an instrument therethrough and to form a fluid-tight seal therewith.

With reference now to FIGS. 1 and 2, obturator member 40 includes an elongate body 42 having a proximal portion 44, a central portion 46, and a distal portion 48. Proximal portion 44 of elongate body 40 includes an actuation member 50 configured for manipulation by a surgeon or other physician to advance or withdraw obturator member 40 through access device 20. Distal portion 48 may include a blunt tip 52 or, in alternative embodiments, may include a blade (not shown) for piercing tissue.

Central portion 46 includes a first recess 54, a second recess 56, and a third recess 58. First recess 54 defines a diameter "$D_1$" and a length "$L_1$," second recess 56 defines a diameter "$D_2$" and a length "$L_2$," third recess defines a diameter "$D_3$" and a length "$L_3$," and elongate body 42 defines a diameter "$D_E$." In an embodiment, diameters "$D_1$," "$D_2$" and "$D_3$" are the same size and are each smaller than diameter "$D_E$". In another embodiment, one or more of diameters "$D_1$," "$D_2$" and "$D_3$" is smaller than one or more of the other diameters "$D_1$," "$D_2$" and "$D_3$" and each of diameters "$D_1$," "$D_2$" and "$D_3$" is smaller than diameter "$D_E$." For example, diameter "$D_1$" may be smaller than diameter "$D_2$" and/or diameter "$D_3$," diameter "$D_2$" may be smaller than diameter "$D_1$" and/or diameter "$D_3$," or diameter "$D_3$" may be smaller than diameter "$D_1$" and/or diameter "$D_2$". Lengths "$L_1$," "$L_2$" and "$L_3$" may be the same size or one or more of lengths "$L_1$," "$L_2$" and "$L_3$" may be larger or smaller than the other lengths "$L_1$," "$L_2$" and "$L_3$." It is contemplated that central portion 46 may include additional recesses or that central portion 46 may include a smaller number of recesses.

Figure 3A:
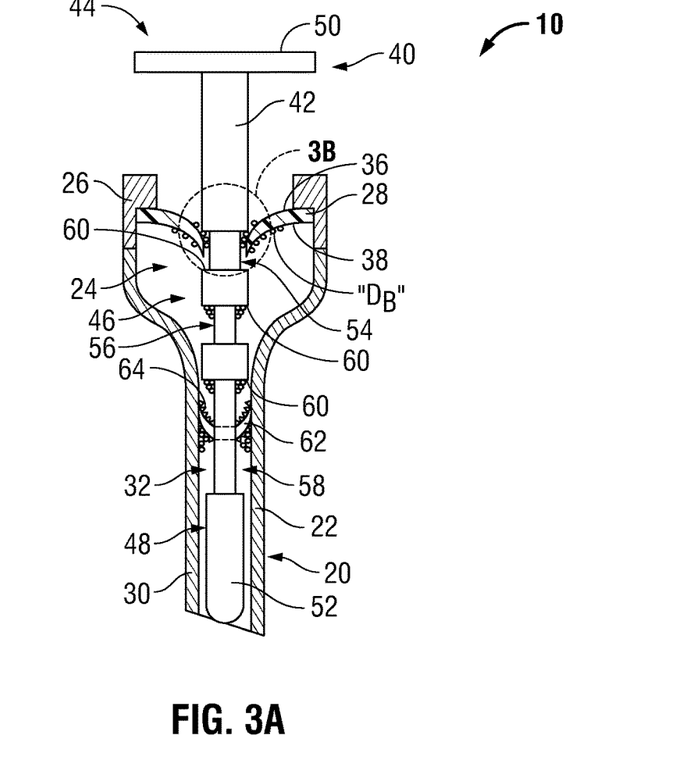
FIG. 3A is a side, cross-sectional view of the access system of FIG. 1, illustrating the obturator member being inserted into the access device.
Figure 3B:
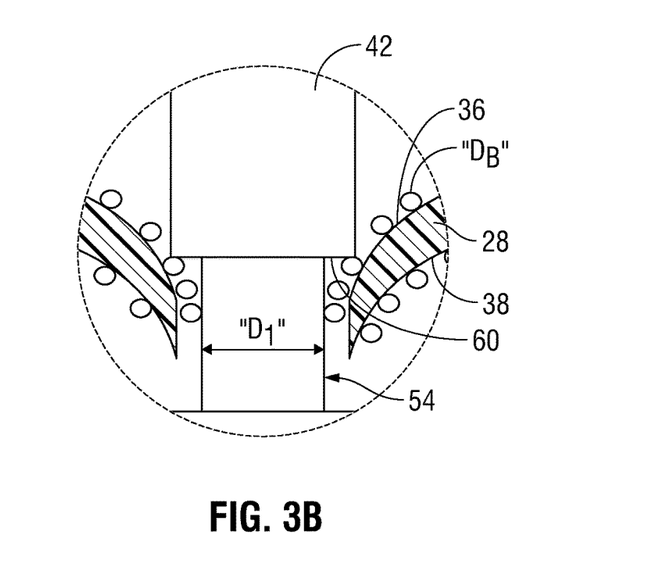
FIG. 3B is an enlarged view of the area of detail "3B" depicted in FIG. 3A, illustrating a recess engaging the proximal surface of the seal member.

With reference now to FIGS. 1, 3A, 3B, 4A and 4B, each of recesses 54, 56, 58 extends circumferentially about central portion 46 and includes corners or edges 60 configured to engage access device 20 to remove debris therefrom. It is also contemplated that each recess 54, 56, 58 may extend only partially about central portion 46 and that recesses 54, 56 and 58 may be circumferentially offset relative to one another. As illustrated in FIGS. 3A and 3B, corners 60 are configured to engage seal member 28 during insertion therethrough and withdrawal therefrom to thereby remove debris "$D_B$" and retain the debris "$D_B$" within recesses 54, 56, 58. Debris "$D_B$" may accumulate in access device 20 and on seal member 28 due to, e.g., insertion and withdrawal of surgical instruments through access device 20 during a surgical procedure. Debris "$D_B$" may also accumulate in access device 20 or on seal member 28 during the insertion of access device 20 through a body tissue opening, natural orifice, or incision.

With reference now to FIGS. 1, 2, 5A and 5B, one or more of recesses 54, 56, 58 includes a flexible member 62 attached thereto. Flexible member 62 may include protrusions 64 configured for engaging and capturing debris therein and may be formed of an absorbent material such as, e.g., urethane, thermoplastic elastomers (TPE), silicone, starch foams, woven or braided structures, and textiles, configured to receive and retain or absorb debris "$D_B$" from access device 20 and seal member 24. Flexible member 62 may also be configured to dispense cleaning solutions into access device 20 to assist in cleaning the interior of access device 20. Flexible member 62 is configured to bend or deform such that flexible member 62 may be received within its respective recess 54, 56, or 58 and may be biased radially outward from its respective recess 54, 56, or 58. Flexible member 62 is configured for insertion through elongate shaft 32 of distal portion 30 of access member 20 during insertion of obturator member 40 through passageway 24 such that flexible member 62 engages the sides 34 of elongate shaft 32 to thereby remove debris "$D_B$" from elongate shaft 32. Flexible member 62 is also configured to engage seal member 28 during insertion or withdrawal of obturator member 40 to remove debris from seal member 28. Flexible member 62 may also be releasably attached to a respective recess 54, 56, or 58 such that flexible member 62 may be replaced during use with a new or clean flexible member 62. For example, a surgeon may withdrawn obturator 40 from access device 20 and replace flexible member 62 with a new flexible member 62 before re-inserting obturator 40 into access device 20 to continue cleaning access device 20

Figure 2A:
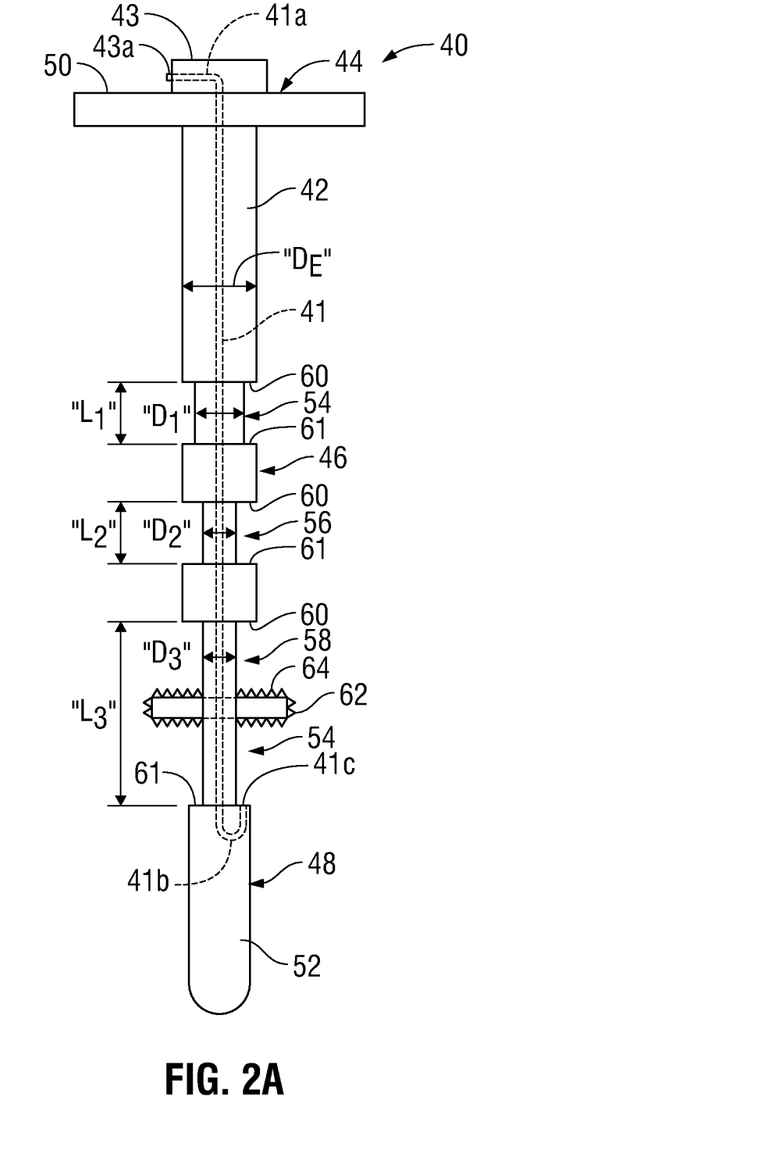
FIG. 2A is a side, partial cross-sectional view of an obturator of the access system of FIG. 1, illustrating a fluid lumen extending through an obturator.

With reference now to FIG. 2A, obturator member 40 may include a fluid lumen 41 extending through elongate body 42 from proximal portion 44 to distal portion 48. Fluid lumen 41 may be configured to supply a fluid solution, e.g., a saline solution or a cleaning solution to access device 20, or may be configured to provide suction. Fluid lumen 41 includes a proximal end 41a fluidly coupled to a connector 43 disposed adjacent proximal portion 44. Connector 43 includes a nozzle 43a configured to fluidly connect to a suction or fluid source (not shown). A distal end portion 41b of fluid lumen 41 may be curled or curved such that a distal opening 41c of fluid lumen 41 is disposed on a distal edge 60 of third recess 58. In this manner, suction and/or a fluid solution may be supplied distal of flexible member 62.

Suction or fluid supply to fluid lumen 41 may be actuated by the motion or pressure created by flexible member 62 or central portion 46 as the flexible member 62 or central portion 46 passes through the seal member 28. For example, engagement of flexible portion 62 or central portion 46 with seal member 28 may transfer pressure or press against fluid lumen 41 to cause fluid lumen 41 to deliver the fluid solution into the access device 20 distal of seal member 28.

With reference now to FIGS. 3A-5B, the use of surgical access system 10 will now be discussed. During a surgical procedure, a surgeon inserts access member 20 into an opening in a patient's body. The opening may be a naturally occurring orifice or may instead be an incision created by the surgeon. Once access device 20 is in place, the surgeon inserts obturator member 40 into passageway 24 of access device 20 through seal member 28.

With reference now to FIGS. 3A and 3B, during insertion of obturator member 40 into access device 20, elongate body 42 is inserted through seal member 28 and into passageway 24. Distal portion 48 of elongate body 42 is inserted through elongate shaft 32 of housing body 22 such that blunt tip 52 extends distally from passageway 24. In an embodiment it is contemplated that elongate body 42 is only partially inserted through passageway 24 such that blunt tip 52 does not extend distally from passageway 24. In an embodiment it is contemplated that obturator member 40 may be inserted into access device 20 prior to insertion of access device 20 into the opening in the patient's body such that the blunt tip 52 or blade (not shown) of elongate body 42 may be used to dissect or penetrate tissue.

As obturator member 40 is inserted through access device 20, flexible member 62 and proximal corners 60 of recesses 54, 56, 58 engage a proximal surface 36 of seal member 28 to scrape and/or remove debris "$D_B$" from proximal surface 36. The removed debris "$D_B$" is retained within recesses 54, 56, 58 adjacent the proximal corners 60. Flexible member 62 is inserted into elongate shaft 32 and engaged against sides 34 of elongate shaft 32 to scrape and remove debris "$D_B$" from elongate shaft 32.

Figure 4A:
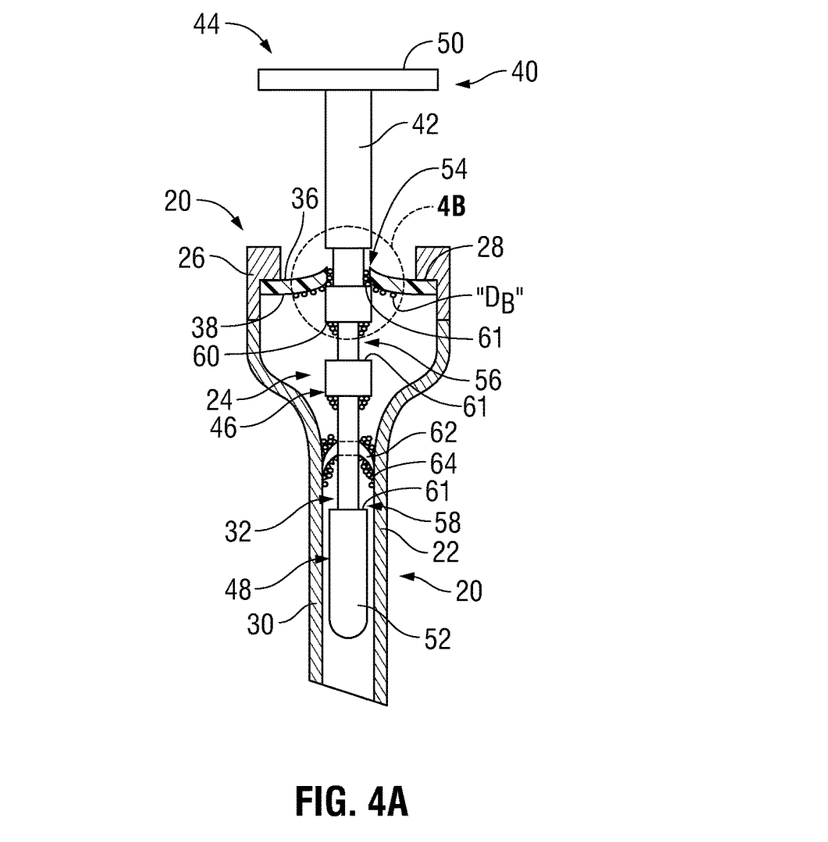
FIG. 4A is a side, partial cross-sectional view of the access system of FIG. 1, illustrating the obturator member being removed from the access device.
Figure 4B:
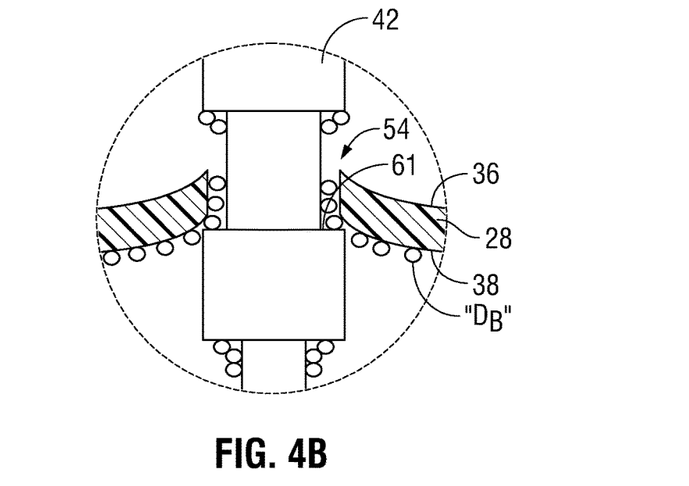
FIG. 4B is an enlarged view of the area of detail "4B" depicted in FIG. 4A, illustrating a recess engaging the distal surface of the seal member.
Figure 5A:
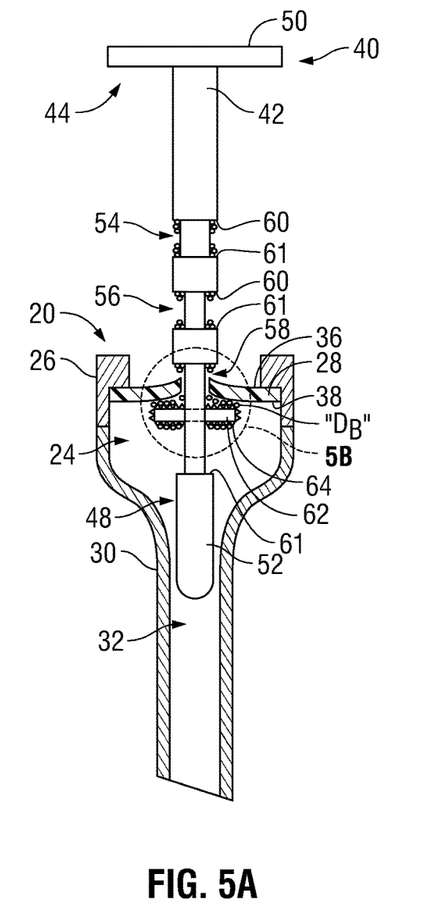
FIG. 5A is a side, partial cross-sectional view of the access system of FIG. 1, illustrating the obturator member being removed from the access device.
Figure 5B:
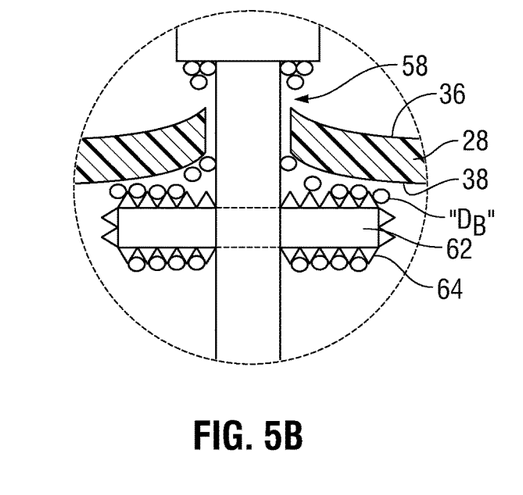
FIG. 5B is an enlarged view of the area of detail "5B" depicted in FIG. 5A, illustrating a flexible member engaging the distal surface of the seal member.

With reference now to FIGS. 4A, 4B, 5A and 5B, with one or more of recesses 54, 56, 58 inserted through seal member 28 and with flexible member 62 engaged against the sides 34 of elongate shaft 32, obturator member 40 is ready to be withdrawn. During withdrawal, flexible member 62 continues to engage and clean sides 34 of elongate shaft 32 either by collecting debris "$D_B$" with protrusions 64 or by absorbing debris "$D_B$" with the absorbent material. In addition, debris "$D_B$" is collected within recesses 54, 56, 58 adjacent distal corners 61. As obturator member 40 withdraws from access device 20, the distal corner 61 of each recess 54, 56, 58 engages, and scrapes, a distal surface 38 of seal member 28, as illustrated in FIG. 4B, to capture and remove debris "$D_B$" from distal surface 38 of seal member 28. Flexible member 62 and protrusions 64 also engage the distal surface 38 of seal member 28, as illustrated in FIG. 5B, to further clean and remove debris "$D_B$" from seal member 28. During withdrawal of obturator member 40, the removed debris "$D_B$" is retained within recesses 54, 56 and 58 and on flexible member 62 and thereby removed from access device 20.

As mentioned above, recesses 54, 56 and 58 may have different diameters which correspond to the depth of each recess 54, 56, 58 relative to the diameter of elongate body 42. For example, a smaller diameter recess 54, 56, or 58 has a larger volume or space in which to capture and retain debris "$D_B$" from access device 20 and may therefore retain larger pieces of debris "$D_B$." In contrast, a smaller diameter recess 54, 56, or 58 has a smaller volume or space in which to capture and retain debris "$D_B$" and may therefore be used to retain finer or smaller portions of debris "$D_B$." By utilizing an obturator member 40 with recesses 54, 56, 58 having diameters of varying size a surgeon can remove and retain both large and small debris "$D_B$" more effectively.

With reference now to FIGS. 6-9, in another embodiment, which is similar to the above embodiment, an obturator member is generally shown as 140. Obturator member 140 includes an elongate body 142 having a proximal portion 144, a central portion 146, and a distal portion 148. Similar to obturator member 40, proximal portion 144 of obturator member 140 includes an actuation member 150 and distal portion 148 of obturator member 140 includes a blunt tip 152 or a blade (not shown). For brevity, only the differences between obturator member 40 and obturator member 140 will be described below in detail.

Figure 7:
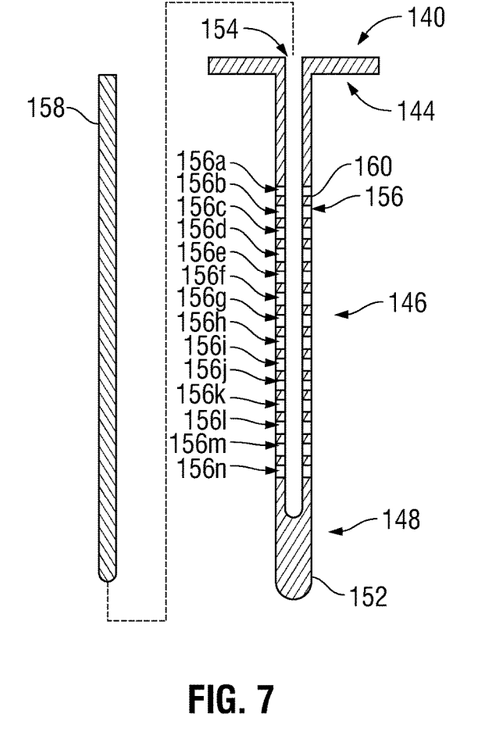
FIG. 7 is side, cross-sectional view of the obturator member of FIG. 6, illustrating the insert member removed.
Figure 8A:
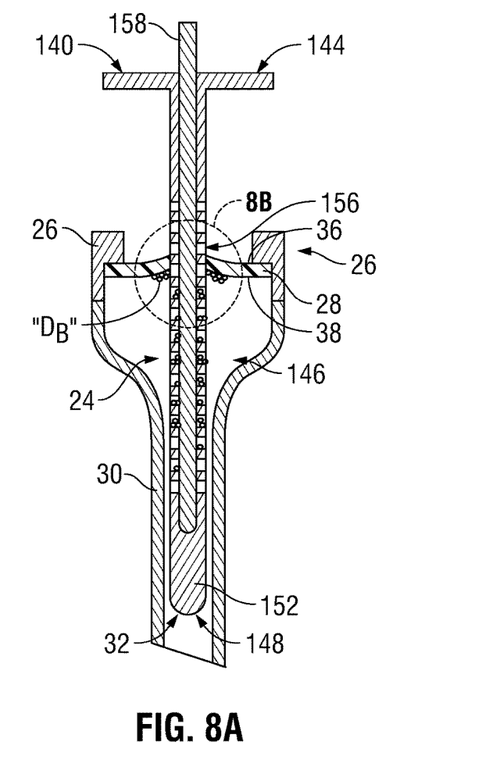
FIG. 8A is side, cross-sectional view of the obturator member of FIG. 6 inserted into the access device of FIG. 1.
Figure 8B:
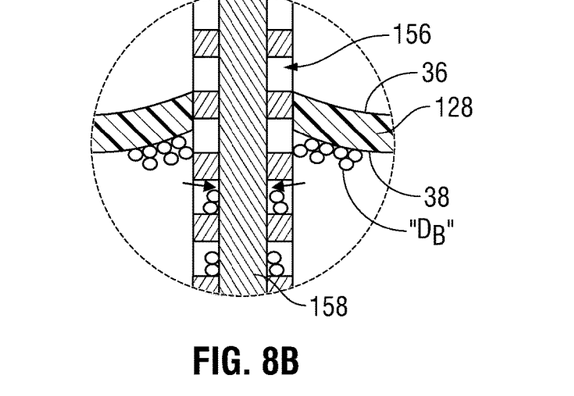
FIG. 8B is an enlarged view of the area of detail "8B" depicted in FIG. 8A, illustrating a plurality of slots engaging the seal member.

With reference now to FIG. 7, elongate body 142 of obturator member 140 includes a central shaft 154 extending therethrough. In an embodiment, central shaft 154 extends through elongate body 142 from proximal portion 144 to distal portion 148. In another embodiment, central shaft 154 extends only partially through elongate body 142, for example, from proximal portion 144 to central portion 146. Elongate body 142 further includes a plurality of slots 156 extending radially therethrough from central shaft 154. Each slot 156 is in fluid communication with central shaft 154 such that fluids and/or solids may travel through slots 156 to enter into central shaft 154. As illustrated in FIGS. 8A and 8B, plurality of slots 156 are configured for engaging access member 20 and seal member 28 to remove debris "$D_B$" therefrom. The debris "$D_B$" removed from access member 20 and seal member 28 is received and retained within plurality of slots 156 and within central shaft 154 for removal from access member 20. Similar to recesses 54, 56 and 58 above, plurality of slots 156 may include corners 160 configured for engaging and scraping debris "$D_B$" from proximal and distal surfaces 36, 38 of seal member 28.

Figure 6:
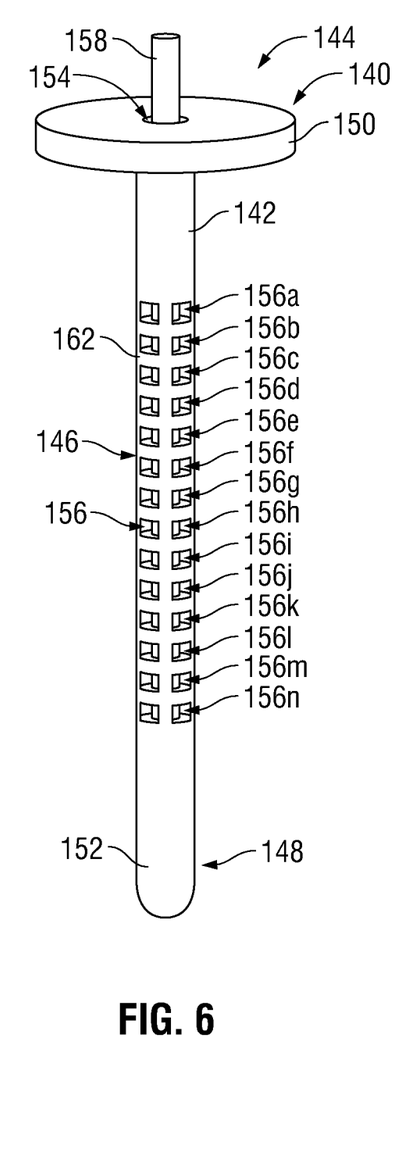
FIG. 6 is a side, perspective view of an obturator member in accordance with an alternate embodiment of the present disclosure.
Figure 9:
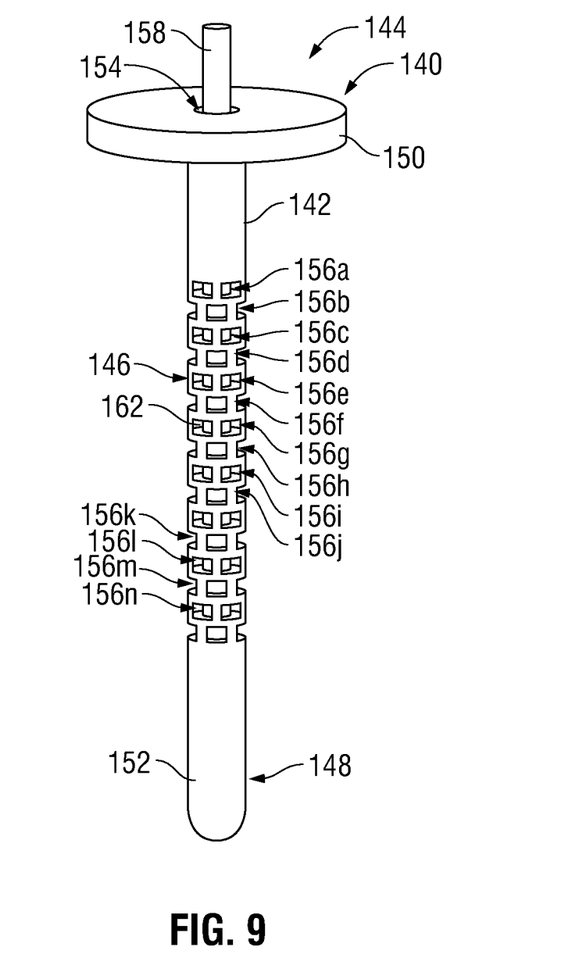
FIG. 9 is a side, perspective view of an obturator member in accordance with an embodiment of the present disclosure.
Figure 10A:
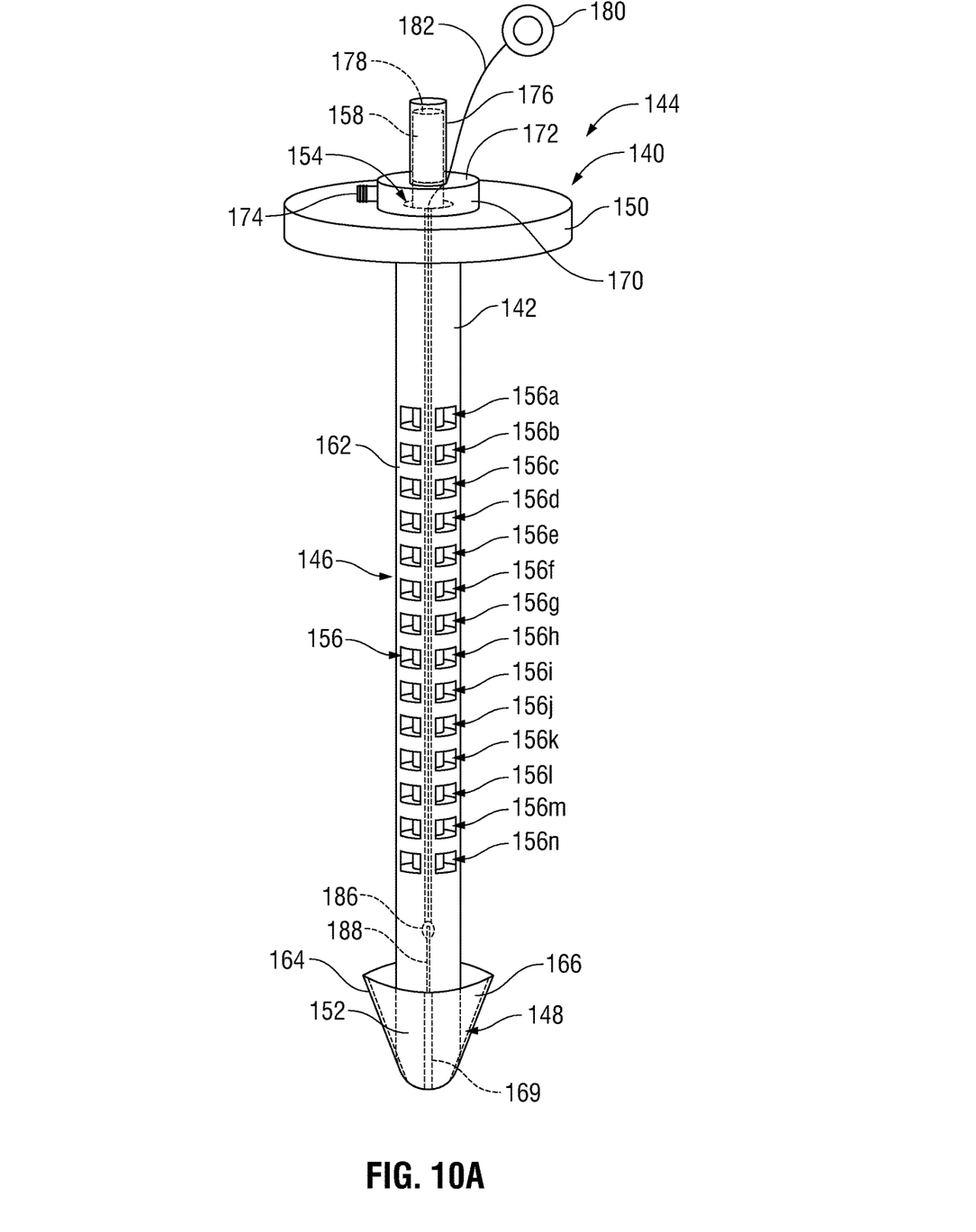
FIG. 10A is a side, perspective view of an obturator member in accordance with an embodiment of the present disclosure including a suction mechanism and an umbrella seal.
Figure 10B:
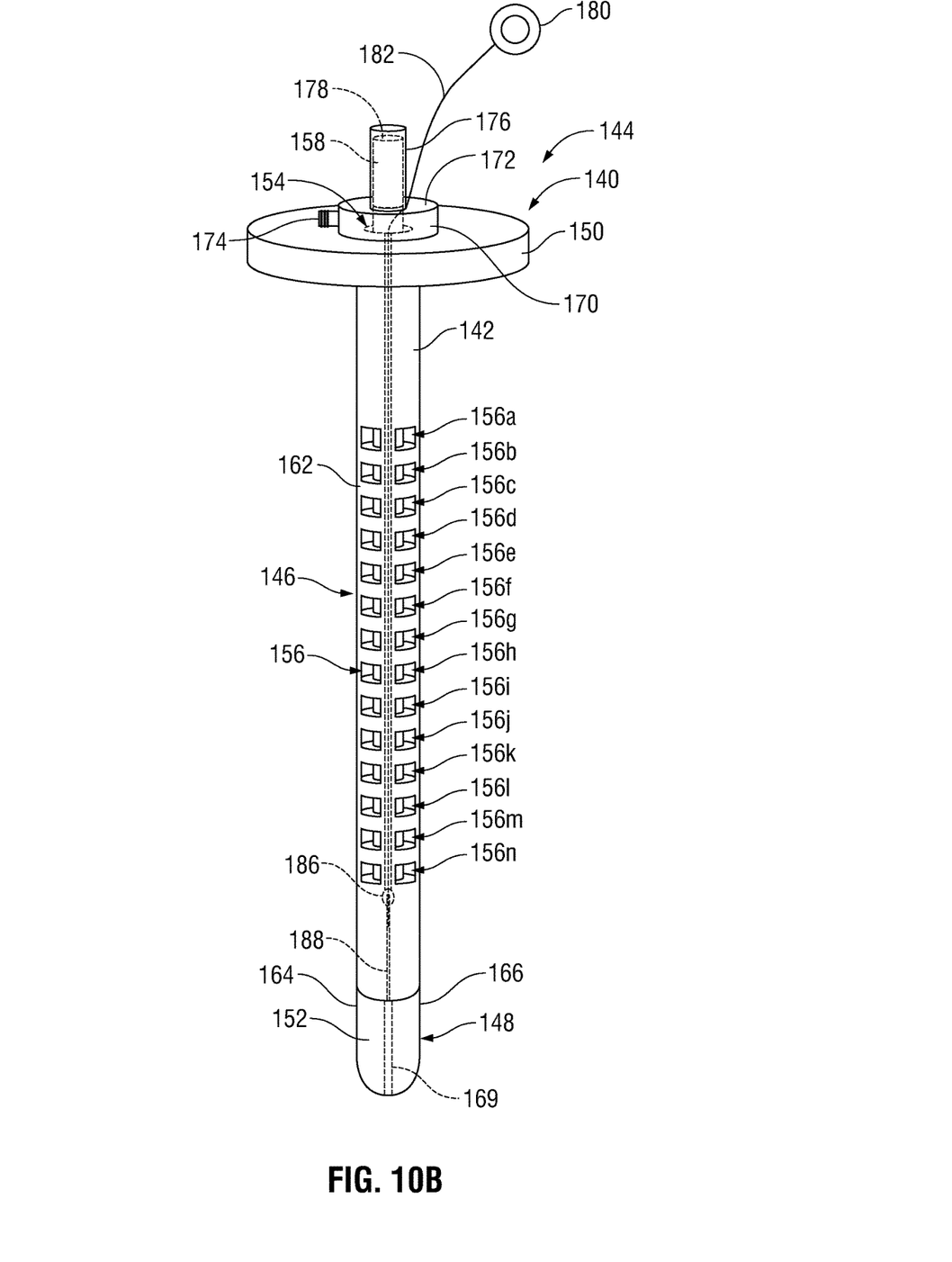
FIG. 10B is a side, perspective view of the obturator member of FIG. 10A with the umbrella seal in a collapsed condition.
Figure 10C:
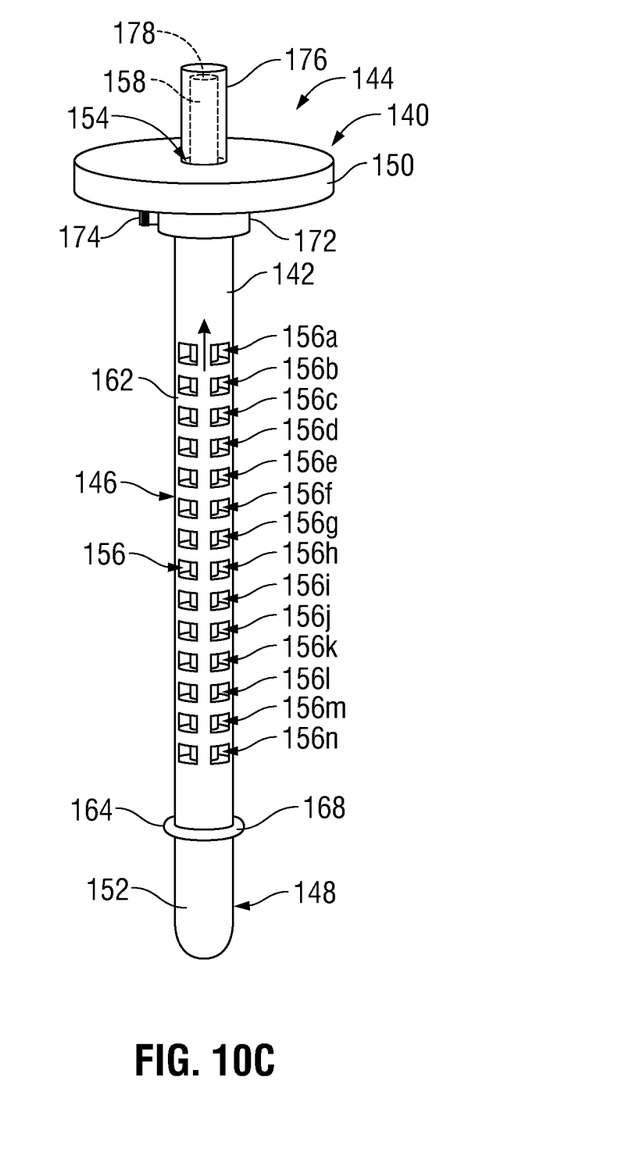
FIG. 10C is a side, perspective view of an obturator member in accordance with an embodiment of the present disclosure including a suction mechanism and a ring seal.
Figure 11A:
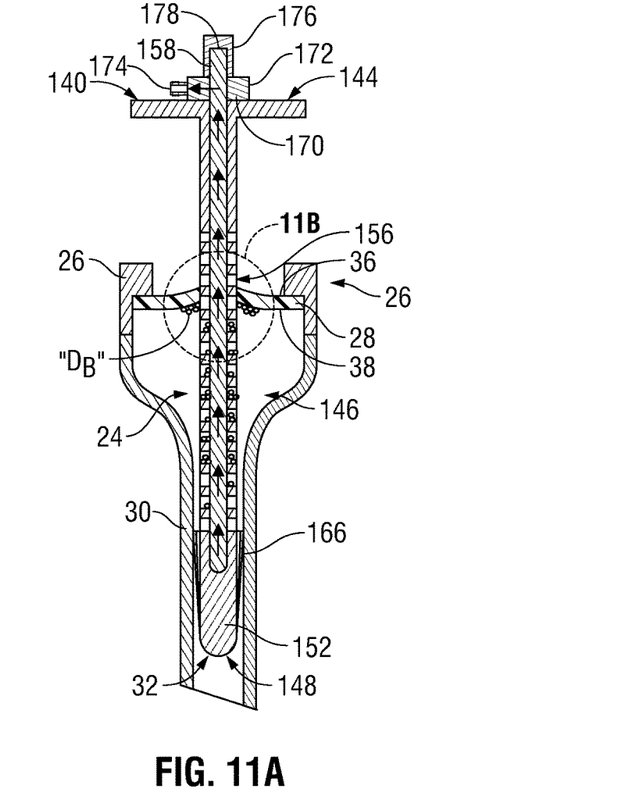
FIG. 11A is side, cross-sectional view of the obturator member of FIG. 10A inserted into an access device.
Figure 11B:
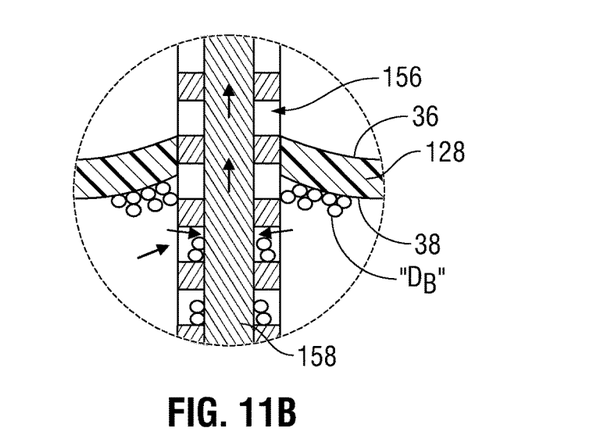
FIG. 11B is an enlarged view of the area of detail "11B" depicted in FIG. 11A, illustrating a plurality of slots engaging the seal member.

As illustrated in FIGS. 6, 7 and 9, plurality of slots 156 extend through elongate body 142 and define bridges 162 in elongate body 142. Bridges 162 provide support to elongate body 142. The position of the plurality of slots 156 can be defined by tiers or levels 156a-156n (FIGS. 6, 7 and 9) where 156a is the proximal most recess tier and 156n is the distal most recess tier. Each tier or level 156a-156n is supported by at least one bridge 162. In an embodiment, for example, each tier or level 156a-156n has four bridges 162 with the slots 156 of the respective tier extending therebetween. In addition, as illustrated in FIG. 9, bridges on adjacent tiers 156a-156n may be rotationally offset such that bridges 162 are not aligned. For example, bridges on tier 156c may be forty-five degrees offset from the bridges on tiers 156d. This ensures that at least one of the plurality of slots 156 will be able to engage seal member 28 as obturator member 140 is inserted and withdrawn from access member 20 even at a location where a bridge 162 may be present. Although slots 156a-156n are illustrated in the figures, it is contemplated that any number of slots 156 may be included without departing from the scope of the present disclosure.

With reference now to FIGS. 7, 8A and 8B, obturator member 140 further includes an insert member 158 configured for removable insertion into central shaft 154 of elongate body 142. Insert member 158 may be formed of an absorbent material that is configured to receive and absorb debris "$D_B$" from access device 20 via the plurality of slots 156 (FIG. 8B). For example, insert member 158 may be utilized to absorb liquid debris from access device 20 while plurality of slots 156 and central shaft 154 retain solid debris from access device 20.

With reference now to FIGS. 8A and 8B, during use, insert member 158 may be inserted into obturator member 140 prior to or after obturator member 140 is inserted into access device 20. In addition, insert member 158 may be removed during use and replaced with a new insert member 158 if there is an excessive amount of debris "$D_B$" in access device 20 to be removed.

Obturator member 140 is inserted through access device 20 in the same manner as obturator member 40, as described above, with plurality of slots 156 engaging seal member 28 to remove debris "$D_B$" from seal member 28. As described above, as obturator member 140 is inserted into and removed from access device 20, plurality of slots 156 collect, remove, and retain debris "$D_B$" from access device 20 and seal member 28. Liquid debris may flow through plurality of slots 156 and into central shaft 154 to be absorbed by insert member 158 while solid debris may be received and retained within plurality of slots 156 and central shaft 154. As with recesses 54, 56 and 58 above, corners 160 of plurality of slots 156 may engage and scrape against proximal and distal surfaces 36, 38 of seal member 28 and/or sides 34 of elongate shaft 32 to remove debris "$D_B$" therefrom.

With reference now to FIGS. 10A-11B, obturator member 140 may include a seal member 164 disposed adjacent distal portion 148 of elongate body 142 for engaging the elongate shaft 32 of housing body 22. For example, seal member 164 may form a fluid tight seal with elongate shaft 32 to prevent or inhibit the escape of insufflation during use of obturator member 140. Seal member 164 may, for example, be an umbrella seal 166 (FIGS. 10A and 10B) or a ring seal 168 (FIG. 10B).

Umbrella seal 166 may be transitionable between a deployed condition (FIG. 10A), where a proximal end of umbrella seal 166 is spaced from obturator member 140 to engage elongate shaft 32 (FIG. 11A) and a collapsed condition (FIG. 10B) where umbrella seal 166 is substantially aligned with or flat against obturator member 140. Umbrella seal 166 may include struts 169 (FIG. 10A) extending therealong which are actuatable to transition the proximal end of umbrella seal 166 between the deployed and collapsed conditions. For example, umbrella seal 166 may be transitionable from the deployed condition to the collapsed condition upon proximal translation of an actuation member 180 (e.g., a pull ring). A wire 182 extends from actuation member 180 through obturator 140 to an eye ring 186. A pull rod 188 extends from eye ring 186 and is coupled to struts 169 such that upon proximal translation of pull rod 188, struts 169 transition the umbrella seal 166 to the collapsed condition. Umbrella seal 166 may be biased toward the deployed condition. Alternatively, umbrella seal 166 may be transitioned between the deployed and collapsed condition by translation of the insert 158 distally to engage a deployment mechanism (FIG. 10A) associated with struts 169 (e.g., a button or pressure activated plate) to cause struts 169 to deploy or collapse the proximal end of the umbrella seal 166. Umbrella seal 166 may also serve in a manner similar to recesses 156 to collect debris "$D_B$" from access device 20 when in the deployed condition. Ring seal 168 may be inflatable or expandable to engage elongate shaft 32. It is contemplated that umbrella seal 166 or ring seal 168 may be deployed through rotation of actuation member 150 or another member relative to central shaft 154.

Obturator member 140 may include a suction mechanism 170 having a suction hookup 172, e.g., a stopcock 174 or other similar attachment component, adjacent actuation member 150 and disposed in fluid communication with central shaft 154 of obturator member 140. For example, suction hookup 172 may be disposed proximal of actuation member 150 (FIG. 10A), distal of actuation member 150 (FIG. 10B), or may be formed as part of actuation member 150. Suction hookup 172 is configured to fluidly couple to a vacuum source (not shown) for providing suction, e.g., negative pressure, to insert member 158 to draw fluid through insert member 158 and out of obturator member 140. Suction mechanism 170 may include a filter or fluid debris collector (not shown) attached between suction mechanism 170 and the vacuum source to inhibit contamination of the vacuum source. Suction mechanism 170 may also assist in drawing debris into slots 156 and insert member 158 from access device 20. Insert member 158 may be formed of a substantially porous material and may include a sealing cap 176 on a proximal end 178 for engaging actuation member 150 or suction mechanism 170 in a substantially fluid tight manner. Sealing cap 176 inhibits air from being drawn through the proximal end 178 of insert member 158 during use. Umbrella seal 166 may be used to seal the body cavity from the vacuum created by the vacuum source (not shown) when suction mechanism 170 is in use. Umbrella seal 166 may also be transitioned between the un-deployed condition and the deployed condition through the use of vacuum.

It is contemplated that any of the above embodiments may be combined without departing from the scope of the present disclosure. For example, obturator 40 may include an insert member, slots, or access channels to transmit debris, a distal sealing member, e.g. an umbrella seal or ring seal, a suction mechanism, or any other feature disclosed herein without departing from the scope of the present disclosure. Likewise, obturator 140 may include a fluid line, a wiper, or any other feature disclosed herein without departing from the scope of the present disclosure.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to the precise embodiments described herein, and that various other changes and modifications may be effected by one skilled in the art without departing from the scope or spirit of the present disclosure.

What is claimed is:

1. A surgical instrument configured for insertion through a surgical access device, the surgical instrument comprising:
   a rigid, elongate body including a central passageway extending at least partially therethrough;
   a plurality of slots extending radially outward from the central passageway, the plurality of slots configured to remove debris from a surgical access device during translation of the elongate body therethrough, the plurality of slots and the central passageway configured to retain removed debris therein; and
   an insert member configured for receipt in the central passageway and having an outer surface that is flush with the plurality of slots.

2. A surgical instrument according to claim 1, wherein the insert member is formed from an absorbent material, the absorbent material configured to absorb and retain debris therein.

3. A surgical instrument according to claim 1, wherein the central passageway extends through a proximal end of the elongate body.

4. A surgical instrument according to claim 1, further including a suction mechanism in fluid communication with the central passageway of the elongate body, the suction mechanism configured to draw debris into the central passageway via the plurality of slots.

5. A surgical instrument according to claim 1, further comprising a seal member coupled to the elongate body.

6. A surgical instrument according to claim 5, wherein the seal member is an umbrella seal, the umbrella seal transitionable between a deployed condition and a collapsed condition.

7. A surgical instrument according to claim 6, wherein the umbrella seal includes at least one strut, the at least one strut configured to transition the umbrella seal between the deployed condition and the collapsed condition.

8. A surgical instrument according to claim 6, wherein a proximal end of the umbrella seal is spaced from the elongate body when the umbrella seal is in the deployed condition.

9. A surgical instrument according to claim 6, wherein the surgical instrument further includes an actuation mechanism operatively associated with the umbrella seal, the actuation mechanism configured to transition the umbrella seal between the deployed condition and the collapsed condition.

10. A surgical instrument according to claim 9, wherein the actuation mechanism includes a cable attached to the umbrella seal, the cable actuatable to transition the umbrella seal between the deployed condition and the collapsed condition.

11. A surgical instrument according to claim 1, further comprising a sealing cap configured to fluidly seal a proximal end of the central passageway.

12. A surgical instrument according to claim 1, wherein the slots extend from the central passageway in a plurality of rows.

13. A surgical instrument according to claim 12, wherein the slots of a first of the rows are rotationally offset relative to the slots of a second of the rows.

14. A surgical instrument according to claim 13, wherein the first and second rows are adjacent one another.

15. A surgical instrument according to claim 5, wherein the seal member is located at a distal portion of the elongate body and is operably coupled to an actuation mechanism.

16. A surgical instrument configured for insertion through an access device, the surgical instrument comprising:
    an elongate body defining a central passageway at least partially through a length of the elongate body;
    a plurality of slots extending radially outward from the central passageway and in fluid communication with the central passageway;
    an insert member configured for receipt in the central passageway and having a uniform diameter along its length; and
    a sealing cap configured to fluidly seal a proximal end of the central passageway.

17. A surgical instrument configured for insertion through an access device, the surgical instrument comprising:
    an elongate body defining a central passageway at least partially through a length of the elongate body;
    a plurality of slots extending radially outward from the central passageway and in fluid communication with the central passageway;
    an insert member configured for receipt in the central passageway, the insert member disposed radially inward of the plurality of slots; and
    a seal member coupled to the elongate body.

* * * * *